(12) United States Patent
Zhang et al.

(10) Patent No.: US 11,623,028 B2
(45) Date of Patent: Apr. 11, 2023

(54) ABSORBABLE IRON-BASED ALLOY IMPLANTED MEDICAL DEVICE

(71) Applicant: Biotyx Medical (Shenzhen) Co., Ltd., Shenzhen (CN)

(72) Inventors: Deyuan Zhang, Shenzhen (CN); Haiping Qi, Shenzhen (CN); Wenjiao Lin, Shenzhen (CN); Gui Zhang, Shenzhen (CN); Li Qin, Shenzhen (CN)

(73) Assignee: Biotyx Medical (Shenzhen) Co., Ltd., Shenzhen (CN)

( * ) Notice: Subject to any disclaimer, the term of this patent is extended or adjusted under 35 U.S.C. 154(b) by 0 days.

(21) Appl. No.: 15/766,842

(22) PCT Filed: Jun. 14, 2016

(86) PCT No.: PCT/CN2016/085657
§ 371 (c)(1),
(2) Date: Apr. 9, 2018

(87) PCT Pub. No.: WO2017/107405
PCT Pub. Date: Jun. 29, 2017

(65) Prior Publication Data
US 2018/0280584 A1     Oct. 4, 2018

(30) Foreign Application Priority Data
Dec. 22, 2015 (CN) .......................... 201510979056.0

(51) Int. Cl.
| | | |
|---|---|---|
| A61K 9/00 | (2006.01) | |
| A61K 33/26 | (2006.01) | |
| A61L 27/04 | (2006.01) | |
| A61L 31/08 | (2006.01) | |
| A61L 27/50 | (2006.01) | |
| A61L 27/58 | (2006.01) | |
| A61L 31/02 | (2006.01) | |
| A61L 31/14 | (2006.01) | |
| A61L 31/10 | (2006.01) | |
| A61L 31/06 | (2006.01) | |
| A61L 31/16 | (2006.01) | |

(52) U.S. Cl.
CPC ............ *A61L 31/022* (2013.01); *A61L 31/06* (2013.01); *A61L 31/10* (2013.01); *A61L 31/14* (2013.01); *A61L 31/148* (2013.01); *A61L 31/16* (2013.01); *A61L 2300/41* (2013.01); *A61L 2300/416* (2013.01); *A61L 2300/42* (2013.01); *A61L 2400/18* (2013.01)

(58) Field of Classification Search
CPC .. A61K 33/26; A61K 9/0024; A61K 2300/00; A61K 2002/30062; A61K 2210/0004; A61K 47/547; A61K 31/295; A61L 27/04; A61L 27/047; A61L 27/042; A61L 2300/606; A61L 2300/604; A61L 31/08; A61L 27/58; A61L 31/022; A61L 2300/42; A61L 31/148; A61L 2300/802; A61L 31/16; A61L 2300/416; A61L 2300/102; A61L 27/50; A61L 2800/606; A61L 27/446; A61P 39/04; A61F 2250/0067; A61F 2/86; A61F 2210/0004; A61F 2310/00011
See application file for complete search history.

(56) References Cited

U.S. PATENT DOCUMENTS

| | | | |
|---|---|---|---|
| 10,946,121 B2 | 3/2021 | Liu et al. | |
| 11,020,514 B2 | 6/2021 | Qi et al. | |
| 2006/0186380 A1* | 8/2006 | Walker | C09K 8/54 |
| | | | 252/392 |
| 2006/0229711 A1* | 10/2006 | Yan | B23K 26/0006 |
| | | | 623/1.38 |
| 2007/0172551 A1* | 7/2007 | Thompson | A23L 33/175 |
| | | | 426/72 |
| 2007/0224244 A1 | 9/2007 | Weber et al. | |
| 2007/0270591 A1* | 11/2007 | Ashmead | C07F 15/025 |
| | | | 548/101 |
| 2008/0009938 A1* | 1/2008 | Huang | A61F 2/91 |
| | | | 623/1.38 |
| 2008/0033539 A1 | 2/2008 | Sternberg et al. | |

(Continued)

FOREIGN PATENT DOCUMENTS

| | | |
|---|---|---|
| CA | 2626805 A1 | 5/2007 |
| CN | 100998897 A | 7/2007 |

(Continued)

OTHER PUBLICATIONS

Ashmead. The absorption and metabolism of iron amino acid chelate. Feb. 28, 2001. Archives Latinoamericanos de Nutricion. vol. 51. pp. 13-21. (Year: 2001).*
International Search Report dated Sep. 18, 2016 of corresponding International application No. PCT/CN2016/085657; 2 pgs.
Office Action dated Apr. 26, 2019, in corresponding Chinese Application No. 201510979056.0 including partial machine-generated English language translation; 17 pages.
Ren et al., "theoretical part on inorganic chemistry", Shanghai Donghua University, Jul. 31, 2015, pp. 126-128, China.
Extended European Search Report dated Jun. 26, 2019, including the Supplementary European Search Report and the European Search Opinion, in connection with corresponding EP Application No. 16877218.4 (8 pp.).

(Continued)

*Primary Examiner* — Tracy Liu
(74) *Attorney, Agent, or Firm* — Maier & Maier, PLLC

(57) ABSTRACT

An absorbable implantable medical device made of iron-based alloy, including a base made of iron-based alloy and a complex, wherein the complex includes a complexing agent. In a physiological solution, the base made of iron-based alloy can react with the complexing agent to generate a water-soluble iron complex having solubility in the physiological solution of no less than 10 mg/L. A corrosion product generated after the absorbable implantable medical device made of iron-based alloy is implanted in a human body can be quickly metabolized/absorbed by the body.

8 Claims, No Drawings

(56) References Cited

U.S. PATENT DOCUMENTS

| | | | |
|---|---|---|---|
| 2009/0110644 A1* | 4/2009 | Margel | A61P 29/00 424/9.42 |
| 2010/0076544 A1 | 3/2010 | Hoffmann et al. | |
| 2010/0174367 A1* | 7/2010 | Janko | A61L 31/022 623/11.11 |
| 2011/0034996 A1* | 2/2011 | Borck | A61L 31/143 623/1.46 |
| 2011/0245905 A1 | 10/2011 | Weber et al. | |
| 2011/0268818 A1 | 11/2011 | Barasch et al. | |
| 2011/0276148 A1 | 11/2011 | Li et al. | |
| 2012/0172794 A1* | 7/2012 | Ascher | A61L 31/10 604/93.01 |
| 2015/0342848 A1* | 12/2015 | Bhushan | A01N 57/12 424/411 |
| 2016/0184244 A1* | 6/2016 | Nicolls | A61K 31/4196 424/489 |
| 2016/0272818 A1* | 9/2016 | Morris | C23C 22/68 |

FOREIGN PATENT DOCUMENTS

| | | | | |
|---|---|---|---|---|
| CN | 102228721 A | 11/2011 | | |
| CN | 102271725 A | 12/2011 | | |
| CN | 103301512 A | 9/2013 | | |
| CN | 104587534 A | 5/2015 | | |
| EP | 2407183 A1 * | 1/2012 | | A61L 31/022 |
| EP | 3 398 622 A1 | 11/2018 | | |
| WO | WO-2006061115 A1 * | 6/2006 | | A61L 31/10 |

OTHER PUBLICATIONS

European Office Action dated Jul. 1, 2021, in connection with corresponding EP Application No. 16 877 218.4; 5 pages.

Extended European Search Report dated Sep. 6, 2021, of corresponding Europe application No. 18897786.2; 7 pages.

Indian Examination Report dated Jul. 21, 2020, of corresponding Indian Application No. 202027031155; 5 pages with English translation.

* cited by examiner

ABSORBABLE IRON-BASED ALLOY IMPLANTED MEDICAL DEVICE

FIELD

The present application belongs to the field of absorbable implanted medical devices, and more particularly relates to an absorbable iron-based alloy implanted medical device.

BACKGROUND

At present, matrix materials for an absorbable implanted medical device mainly include polymers, a magnesium-based alloy and an iron-based alloy. The most frequently applied polymer is polylactic acid, which can be completely degraded and absorbed, with degradation products of carbon dioxide and water, but its mechanical properties are poor. The size of the polymer-based device should be larger than the metal-based device so that the polymer-based device can have the same mechanical properties as the metal-based device, which limits application of the polymer-based device. The magnesium-based alloy and the iron-based alloy have advantages of easiness in processing, molding, and high mechanical strengths. However, as the magnesium-based alloy is corroded too fast in a human body, it is necessary to enlarge the size of a magnesium-based alloy device to obtain the mechanical property in the early stage of implantation, and in this way, the application of the magnesium-based alloy is limited as well.

As a matrix material of the implanted medical device, the iron-based alloy has a good biological compatibility, and its corrosion speed is lower than that of the magnesium-based alloy. On the premise of obtaining the same mechanical properties in the early stage of implantation, the size of the iron-based alloy is smaller than the polymer-based device and the magnesium-based alloy device. However, an insoluble corrosion product would be generated by corrosion of the iron-based alloy material in the body. The volume of the corrosion product is generally 3 to 8 times that of the iron-based alloy substrate and the corrosion product is not quickly absorbed or metabolized by an organ, which can lead to some potential biological risks. Therefore, it is desired to reduce insoluble corrosion products for an iron-based alloy implanted medical device.

SUMMARY

For shortcomings in the prior art, the present application aims to provide an absorbable iron-based alloy implanted medical device. After the absorbable iron-based alloy implanted medical device is implanted into a body, all/part of corrosion products of an iron-based alloy are turned into water-soluble iron complexes which are quickly metabolized/absorbed by an organ. An absorbable iron-based alloy implanted medical device is provided, including an iron-based alloy substrate and a complex body. The complex body includes a complexing agent. In a physiological solution, the iron-based alloy substrate may react with the complexing agent to generate a water-soluble iron complex which has a solubility (metered by iron) greater than or equal to 10 mg/L in the physiological solution.

The complex body may consist of a complexing agent, or further include an adhesive and/or a thickener besides the complexing agent. When the complex body contains other components besides the complexing agent, the volume percent of the complexing agent is greater than or equal to 10 percent, but less than 100 percent.

The complexing agent is a strong field monodentate ligand and/or a polydentate ligand.

The strong field monodentate ligand contains a coordination group which is a cyanide group, thiocyanate (S—C≡N<->), iso-thiocyanate (N=C=S<->) or nitryl (—NO2). The polydentate ligand contains at least two coordination groups selected form the group consisting of hydroxyl on polycyclic aromatic hydrocarbon, sulfydryl (—SH), amido

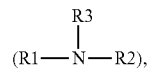

a hetero aromatic group, nitroso (O=N—), carbonyl

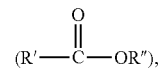

sulpho

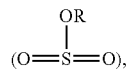

a phosphate group

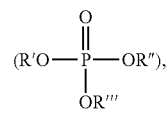

and an organic phosphorus group

The hydroxyl on the polycyclic aromatic hydrocarbon is a phenolic hydroxyl group. The hetero aromatic group is selected from the group consisting of furyl

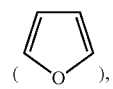

pyrryl

thienyl
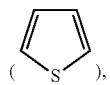
imidazoly
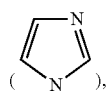
triazolyl
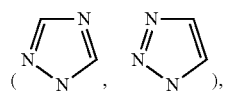
thiazolyl
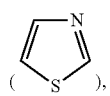
pyridyl
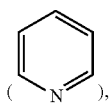
a pyridone group
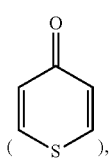
pyranyl
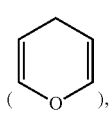
a pyrone group
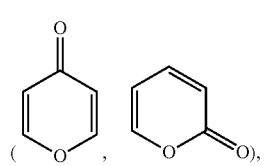
pyrimidyl
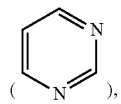
pyridazinyl
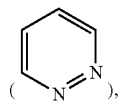
pyrazinyl
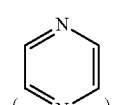
quinolyl
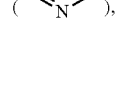
isoquinolyl
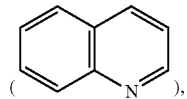
phthalazinyl
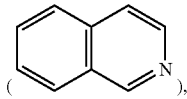
pteridyl
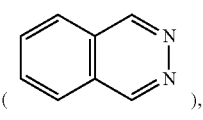

indolyl

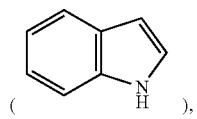

( ), purinyl

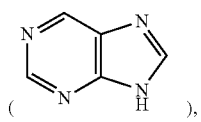

( ), and a phenanthroline group

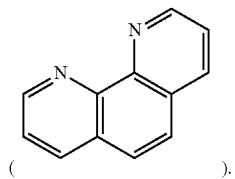

( ).

The cyanide group-containing monodentate ligand is selected from the group consisting of sodium cyanide, zinc cyanide, 3-cyanopyridine, dicyandiamide and palmitonitrile; the thiocyanate-containing monodentate ligand is selected from the group consisting of sodium hydro sulfide, potassium thiocyanate and calcium thiocyanate; the isothiocyanate-containing monodentate ligand is selected from the group consisting of potassium isothiocyanate and isothiocyanate; and the nitryl-containing monodentate ligand is selected from the group consisting of nitrocyclopentane and 2-bromo-2-nitro-1,3-propanediol.

The hydroxyl-on-polycyclic aromatic hydrocarbon-containing polydentate ligand is selected from the group consisting of 8-hydroxyquinoline, 8-hydroxyquinaldine, 4,5-dioxybenzene-1,3-sodium disulfonate, 4-[3,5-bis-hydroxyphenyl-1H-1,2,4-triazole]-benzoic acid (deferasirox); the sulfydryl-containing polydentate ligand is selected from the group consisting of 8-mercaptoquinoline, mercaptoacetic acid and 5-methyl-2 mercapto mercaptobenzoate; the amido-containing polydentate ligand is selected from the group consisting of ethylenediamine, triethylene tetramine, ethylenediamine tetraacetic acid, ethylene diamine tetraacetic acid tetrasodium and N'-[5-[[4-[[5-(acetyl hydroxylamine)amyl]ammonia]-1,4-dioxo butyl]hydroxylamine]amyl]-N-(5-amido amyl)-N-hydroxyl succinamide (deferoxamine); the hetero aromatic group-containing polydentate ligand is selected from the group consisting of phenanthroline, dipyridyl, porphyrin, porphin, chlorophyll, hemoglobin and 1,2-dimethyl-3-hydroxyl-4-pyridone (deferiprone); the nitroso-containing polydentate ligand is selected from the group consisting of 1-nitroso-2-naphthol and 1-nitroso-2-naphthol-6-sodium sulfonate; the carbonyl-containing polydentate ligand is selected from the group consisting of polybasic carboxylic acid and salt thereof, anhydride, ester, amide, polycarboxylic acid and polyanhydride; the sulpho-containing polydentate ligand is selected from the group consisting of sulfosalicylic acid and 8-hydroxyquinoline-5-sulphonic acid; the phosphate group-containing polydentate ligand is selected from the group consisting of pyrophosphoric acid, tripolyphosphoric acid, hexadecophosphoric acid, polyphosphoric acid, sodium pyrophosphate, sodium hexametaphoshpate and ammonium polyphosphate; the organic phosphorus group-containing polydentate ligand is selected from the group consisting of potassium diethylenetriamine penta (methylene phosphonate) and sodium ethylenediamine tetra (methylene phosphonate); the carbonyl-containing polydentate ligand is further selected from the group consisting of oxalic acid, tartaric acid, malic acid, succinic acid, oxaloacetic acid, fumaric acid, maleic acid, citric acid, nitrilotriacetic acid, diethylene triamine penta (carboxylic acid), alginic acid, glutamic acid, aspartic acid, ornithine, lysine, potassium citrate, calcium citrate, monoglyceride citrate, acetylsalicylic acid, sulpho salicylamide, polyaspartic acid, polyglutamic acid, poly-ornithine, polylysine and polymaleic anhydride.

The adhesive is selected from at least one of polyethylene glycol, polyvinyl alcohol, starch, cyclodextrin or water-soluble inorganic salt; and the thickener is selected from at least one of gelatin, polyvinylpyrrolidone (PVP) or sodium carboxymethylcellulose (CMC). The complex body is disposed on the surface of or inside the iron-based alloy substrate. The implanted medical device further includes a degradable polymer layer in which an active drug is mixed, or no active drug is mixed.

The iron-based alloy substrate may be pure iron or an iron-based alloy with a carbon content less than or equal to 2.11 wt. %.

Compared with the prior art, the absorbable iron-based alloy implanted medical device includes the complex body. After the device is implanted into the body, the iron-based alloy substrate is corroded to generate $Fe^{2+}$ or $Fe^{3+}$ under a physiological environment, and complex reaction occurs between $Fe^{2+}$ or $Fe^{3+}$ and the complexing agent, thereby generating the water-soluble iron complex, and the quantity of insoluble solid corrosion products of the iron-based alloy is reduced.

DETAILED DESCRIPTION

In order to facilitate understandings of the present application, the present application provides a preferred embodiment. However, the present application may be implemented by many different forms, not limited by the embodiment described herein. On the contrary, the object of providing these embodiments is to make the disclosed contents of the present application more thorough and comprehensive.

Unless otherwise defined, all technical and scientific terms used herein have the same meanings of general understandings of persons skilled in the art of the present application. Terms used in the description herein are only intended to describe the specific embodiments, but not to limit the present application.

In the present application, an iron-based alloy substrate and a complex body react with each other in a physiological solution to generate a water-soluble iron complex to avoid or reduce generation of insoluble solid corrosion products.

After an iron-based alloy medical device is implanted into a human body, the iron-based alloy substrate is gradually corroded in the physiological solution to generate a primary corrosion product $Fe^{2+}$ or $Fe^{3+}$ which then quickly reacts with $OH^-$ to generate the insoluble corrosion products such as $Fe(OH)_2$ and $Fe(OH)_3$ and to further generate insoluble substances such as FeOOH, $Fe_2O_3$ and $Fe_3O_4$. Reaction equations are as shown in formulas from (1) to (3). With loose structures, these corrosion products may be expanded by 3 to 8 times in volume than the iron-based alloy substrate and are really difficult to dissolve in the physiological solution, so that it would take a very long time for a tissue to metabolize/absorb them, and they would be retained in the tissue for a long time, which may possibly lead to some potential biological risks.

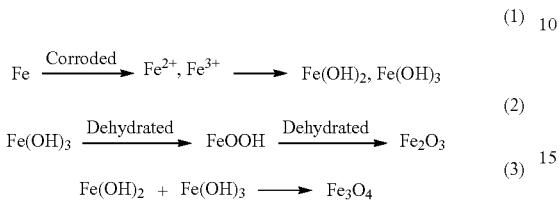

The complexing agent is also called a ligand, which structurally contains a coordination group for lone pair electrons or π electrons. In order to reduce generation of the iron insoluble corrosion products, the complexing agent (which is also called the ligand and abbreviated as L) is disposed in the iron-based alloy implanted medical device. Under a physiological environment, the complexing agent may provide the lone pair electrons or π electrons for a complex reaction with $Fe^{2+}$ and/or $Fe^{3+}$ to generate a water-soluble iron complex. The water-soluble iron complex may be metabolized/absorbed by an organ more quickly than the insoluble solid corrosion products, and its stability is higher than that of $Fe(OH)_2$ and/or $Fe(OH)_3$ and would not be turned into insoluble $Fe(OH)_2$ and/or $Fe(OH)_3$ in the physiological solution. Its reaction equation is as shown in formula (4).

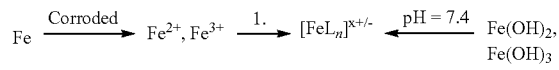

It is defined that the iron complex, of which the solubility in the physiological environment is not lower than 10 mg/L, is called the water-soluble iron complex. In case of the solubility greater than or equal to 100 mg/L in the physiological environment, the iron complex may be quickly diffused and metabolized; in case of the solubility greater than or equal to 10 mg/L but less than 100 mg/L in the physiological environment, although the solubility of such iron complex is lower, complex sedimentation may occur due to saturation of the iron complex concentration in the solution, complex sediments may be continuously and gradually dissolved with gradual diffusion and absorption/metabolism of the dissolved iron complex in the physiological solution, and are finally completely dissolved and diffused and then absorbed/metabolized by the tissue.

The complexing agent is a strong field monodentate ligand and/or a polydentate ligand.

The monodentate ligand easily provides the lone pair electrons which form an inner-orbital complex together with $Fe^{2+}/Fe^{3+}$. The inner-orbital complex has a mechanism which is more stable than an outer-orbital complex and may not be turned into an insoluble substance $Fe(OH)_2$ and/or $Fe(OH)_3$ under a physiological condition.

The monodentate ligand contains a coordination group which is a cyanide group, thiocyanate (S—C≡N<->), isothiocyanate (N=C=S<->) or nitryl (—NO2).

The polydentate ligand contains at least two coordination groups which may form a more stable chelate (an annular structure) together with ions $Fe^{2+}/Fe^{3+}$.

The polydentate coordination group is selected from the group consisting of hydroxyl on polycyclic aromatic hydrocarbon, sulfydryl (—SH), amido

a hetero aromatic group, nitroso (O=N—), carbonyl

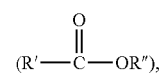

sulpho

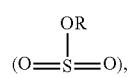

a phosphate group

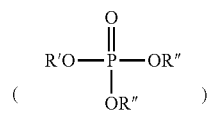

and an organic phosphorus group

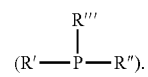

The polydentate ligand may either contain at least two identical coordination groups, or contain different coordination groups.

The hydroxyl on the polycyclic aromatic hydrocarbon is a phenolic hydroxyl group. The hetero aromatic group is selected from furyl

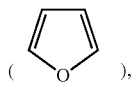

pyrryl

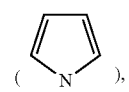

thienyl
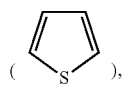
imidazolyl
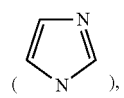
triazolyl
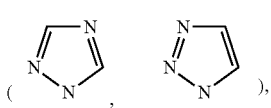
thiazolyl
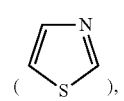
pyridyl
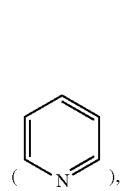
a pyridone group
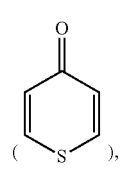
pyranyl
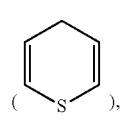
a pyrone group
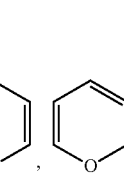
pyrimidyl
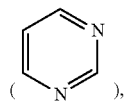
pyridazinyl
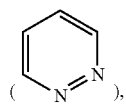
pyrazinyl
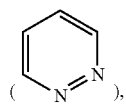
quinolyl
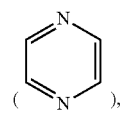
isoquinolyl
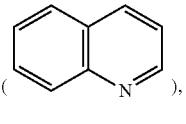
phthalazinyl
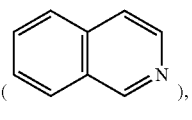
pteridyl
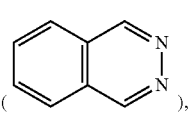
indolyl
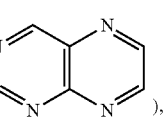

purinyl

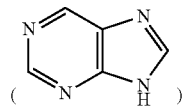

and a phenanthroline group

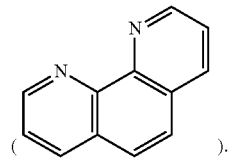 [SMILES: c1cnc2c(c1)ccc1cccnc12]

The cyanide group-containing monodentate ligand is selected from the group consisting of sodium cyanide, zinc cyanide, 3-cyanopyridine, dicyandiamide and palmitonitrile; the thiocyanate-containing monodentate ligand is selected from the group consisting of sodium hydro sulfide, potassium thiocyanate and calcium thiocyanate; the isothiocyanate-containing monodentate ligand is selected from the group consisting of potassium isothiocyanate and isothiocyanate; and the nitryl-containing monodentate ligand is selected from the group consisting of nitrocyclopentane and 2-bromo-2-nitro-1,3-propanediol.

The hydroxyl-on-polycyclic aromatic hydrocarbon-containing polydentate ligand is selected from the group consisting of 8-hydroxyquinoline, 8-hydroxyquinaldine and 4,5-dioxybenzene-1,3-sodium disulfonate, 4-[3,5-bis-hydroxyphenyl-1 H-1,2,4-triazole]-benzoic acid (deferasirox); the sulfydryl-containing polydentate ligand is selected from the group consisting of 8-mercaptoquinoline, mercaptoacetic acid and 5-methyl-2-mercapto mercaptobenzoate; the amido-containing polydentate ligand is selected from the group consisting of ethidene diamine, triethylene tetramine, ethylenediamine tetraacetic acid, ethylene diamine tetraacetic acid tetrasodium and N'-[5-[[4-[[5-(acetyl hydroxylamine)amyl]ammonia]-1,4-dioxo butyl]hydroxylamine] amyl]-N-(5-amido amyl)-N-hydroxyl succinamide (deferoxamine); the hetero aromatic group-containing polydentate ligand is selected from the group consisting of phenanthroline, dipyridyl, porphyrin, porphin, chlorophyll, hemoglobin and 1,2-dimethyl-3-hydroxyl-4-pyridone (deferiprone); the nitroso-containing polydentate ligand is selected from the group consisting of 1-nitroso-2-naphthol and 1-nitroso-2-naphthol-6-sodium sulfonate; the carbonyl-containing polydentate ligand is selected from the group consisting of polybasic carboxylic acid and salt thereof, anhydride, ester, amide, polycarboxylic acid and polyanhydride; the sulpho-containing polydentate ligand is selected from the group consisting of sulfosalicylic acid and 8-hydroxyquinoline-5-sulphonic acid; the phosphate group-containing polydentate ligand is selected from the group consisting of pyrophosphoric acid, tripolyphosphoric acid, hexadecophosphoric acid, polyphosphoric acid, sodium pyrophosphate, sodium hexametaphoshpate and ammonium polyphosphate; the organic phosphorus group-containing polydentate ligand is selected from the group consisting of potassium diethylenetriamine penta (methylene phosphonate) and sodium ethylenediamine tetra(methylene phosphonate); the carbonyl-containing polydentate ligand is further selected from the group consisting of oxalic acid, tartaric acid, malic acid, succinic acid, oxaloacetic acid, fumaric acid, maleic acid, citric acid, nitrilotriacetic acid, diethylene triamine penta(carboxylic acid), alginic acid, glutamic acid, aspartic acid, ornithine, lysine, potassium citrate, calcium citrate, monoglyceride citrate, acetylsalicylic acid, sulpho salicylamide, polyaspartic acid, polyglutamic acid, polyornithine, polylysine and polymaleic anhydride.

The complex body may further include an adhesive and/or a thickener. When the complex body is a complexing agent and adhesive and/or thickener mixture, the volume percent of the complexing agent in the mixture is greater than or equal to 10 percent but less than 100 percent. The adhesive is selected from at least one of polyethylene glycol, polyvinyl alcohol, starch, cyclodextrin or water-soluble inorganic salt; and the thickener is selected from at least one of gelatin, polyvinylpyrrolidone (PVP) or sodium carboxymethylcellulose (CMC). The adhesive makes firmer combination between the complexing agent and the substrate, and the thickener may achieve a slow release effect on the complexing agent.

The amount (weight or volume) of the complex body may be flexibly selected according to the type and the specification of the device and the solubility of the formed iron complex, thereby adjusting the amount of the iron complex generated by reaction with $Fe^{2+}$ or $Fe^{3+}$ formed by corrosion of the iron-based alloy substrate, and fulfilling the aim of adjusting a metabolism/absorption cycle of a corrosion product.

The complex body may be disposed on the surface of or inside the iron-based alloy substrate in ways of spray coating, dip coating, brush coating, electrostatic spinning, 3D printing, embedding, filling and the like.

The implanted medical device further includes a degradable polymer layer. The degradable polymer layer is either disposed on the surface of the iron-based alloy substrate or embedded inside the iron-based alloy substrate. The degradable polymer is selected from degradable polyester and/or degradable polyanhydride. The degradable polyester is any one of polylactic acid, polyglycolic acid, poly(lactic acid-glycolic acid), polycaprolactone, polyhydroxyalkanoate, polyacrylate, poly(ethylene succinate), poly(β-hydroxybutyrate) and polyethylene glycol adipate, or is a physical blend of at least two of the polylactic acid, the polyglycolic acid, the poly(ethylene succinate), the poly(β-hydroxybutyrate), the polycaprolactone, the polyethylene glycol adipate, a polylactic acid-glycollic acid copolymer and a polyhydroxybutyrate-pentanoate copolymer, or is any one of copolymers formed by copolymerizing at least two of monomers forming the polylactic acid, the polyglycolic acid, the poly(ethylene succinate), the poly(β-hydroxybutyrate), the polycaprolactone, the polyethylene glycol adipate, the polylactic acid-glycollic acid copolymer and the polyhydroxybutyrate-pentanoate copolymer. The degradable polyanhydride is selected from at least one of poly1,3-bis(p-carboxyphenoxy)propane-sebacic acid, poly(erucic acid dimer-sebacic acid) or poly(fumaric acid-sebacic acid), or is a physical blend of at least two of the poly1,3-bis(p-carboxyphenoxy)propane-sebacic acid, the poly(erucic acid dimer-sebacic acid) or the poly(fumaric acid-sebacic acid), or any one of copolymers formed by copolymerizing at least two of monomers forming the poly1,3-bis(p-carboxyphenoxy)propane-sebacic acid, the poly(erucic acid dimer-sebacic acid) or the poly(fumaric acid-sebacic acid); or the degradable polymer is a copolymer formed by copolymerizing at least two of monomers forming the above degradable polyester and the above degradable polyanhydride.

The degradable polymer layer further includes an active drug; thus a curative drug may be released in a degradation process. The active drug may be a drug for inhibiting vascular proliferation, such as taxol, sirolimus and its derivative, or an antiplatelet drug such as cilostazol, or an antithrombotic drug such as heparin, or an anti-inflammatory reaction drug such as dexamethasone, or an antisensitization drug such as calcium gluconate, chlortrimeton and cortisone. The active drug also may be a mixture of at least two of the above drugs.

The iron-based alloy substrate may be pure iron or an iron-based alloy with a carbon content less than or equal to 2.11 wt. %, such as a product obtained by nitriding and/or carburizing the pure iron.

The absorbable iron-based alloy implanted medical device may be a blood vessel stent, an orthopedic implant, a gynecological implant, an andrological implant, a respiratory implant or an orthopedic implant.

By taking an iron-based alloy bone nail and an iron-based alloy coronary artery stent as examples, a further detailed description is made to the present application in combination with specific embodiments as follows, but they are not intended to limit the scope of protection of the present application.

In a physiological solution, which may be a saturated solution or a non-saturated solution, with a pH value of 7.4 at 37° C., after an iron complex is corroded in vitro for one week, its concentration in the physiological environment is more than or equal to 10 mg/L, which indicates that the solubility of the iron complex is more than or equal to 10 mg/L. The concentration of the iron complex in the physiological environment is measured in a way as follows: under a condition of 37° C., soaking a complex body-containing medical device in a phosphate buffer solution (PBS), which is 5 times the volume of the device, for an in-vitro corrosion experiment; after the medical device is corroded in the PBS for one week, filtering the soaking solution with a water-based film having an aperture of 0.22 μm; and then testing the mass concentration of an iron element dissolved in filtrate with an atomic absorption spectrometer (AAS), thereby obtaining the concentration of the iron complex in the physiological environment.

It should be noted that in each embodiment as follows, a normal fluctuation of the performance of a product within a designed allowable range, a difference of an individual corrosion speed of the device, and a system error unavoidably introduced by testing ways may lead to fluctuations of detected concentrations of the iron complex within a certain range in an actual test.

Embodiment 1

A stent is manufactured in a way of 3D printing. A material for a stent substrate is pure iron, and a groove is formed in the surface of the stent and is filled with an ethylene diamine tetraacetic acid tetrasodium and polyvinylpyrrolidone mixed coating, wherein a mass ratio of ethylene diamine tetraacetic acid tetrasodium to polyvinylpyrrolidone to iron is 0.1 to 0.1 to 1; and the outermost layer of the stent is coated with a poly-dl-lactic acid coating which has a molecular weight of 200,000 and a thickness of 4 μm. The stent is soaked in the PBS, which is 5 times the volume of the stent, at 37° C. After the stent is corroded in vitro for one week, a formed iron complex is fully dissolved in the solution, then the soaking solution is filtered with the water-based filtering film having the aperture of 0.22 μm, and the concentration of dissolved iron in filtrate is tested with the atomic absorption spectrometer, thereby the concentration of the iron complex in the physiological environment is 186 mg/L.

Embodiment 2

Micro pores in the surface of a hollow pure iron bone nail are filled with sodium pyrophosphate to manufacture an absorbable iron-based bone nail. A mass ratio of the sodium pyrophosphate to iron is 0.5 to 1. The bone nail is soaked in the PBS, which is 5 times the volume of the bone nail, at 37° C. After the bone nail is corroded in vitro for one week, a formed ferric pyrophosphate complex is fully dissolved in the solution, then the soaking solution is filtered with the water-based filtering film having the aperture of 0.22 μm, and the concentration of dissolved iron in filtrate is tested with the atomic absorption spectrometer, thereby the concentration of the ferric pyrophosphate complex in the physiological environment is 24 mg/L.

Embodiment 3

The surface of a pure iron stent is coated with a calcium citrate and polyethylene glycol mixed coating, which has a thickness of 5 μm, in a way of spraying coating, and a mass ratio of calcium citrate to polyethylene glycol is 2 to 1. Then a poly-dl-lactic acid-ethyl acetate (-sirolimus) solution having a molecular weight of 200,000 completely covers the surface of the stent in the way of spray coating, and after the surface is dried, an absorbable iron-based alloy stent with a poly-dl-lactic acid (-sirolimus) coating having a thickness of 5 μm is manufactured, wherein a mass ratio of poly-dl-lactic acid to sirolimus is 4 to 1. The stent is soaked in the PBS, which is 5 times the volume of the stent, at 37 ° C. After the stent is corroded in vitro for one week, a formed iron gluconate complex is fully dissolved in the solution, then the soaking solution is filtered with the water-based filtering film having the aperture of 0.22 μm, and the concentration of dissolved iron in filtrate is tested with the atomic absorption spectrometer, thereby the concentration of the ferric citrate complex in the physiological environment is 113 mg/L.

Embodiment 4

Micro pores in the surface of a hollow pure iron bone nail are filled with a palmitonitrile and polyvinylpyrrolidone mixture to manufacture an absorbable iron-based bone nail. A mass ratio of palmitonitrile to polyvinylpyrrolidone to iron is 0.25 to 0.25 to 1. The bone nail is soaked in the PBS, which is 5 times the volume of the bone nail, at 37° C. After the bone nail is corroded in vitro for one week, a formed palmitonitrile iron complex is fully dissolved in the solution, then the soaking solution is filtered with the water-based filtering film having the aperture of 0.22 μm, and the concentration of dissolved iron in filtrate is tested with the atomic absorption spectrometer, thereby the concentration of the palmitonitrile iron complex in the physiological environment is 47 mg/L.

Embodiment 5

The surface of a pure iron stent is coated with an acetylsalicylic acid-chloroform solution in a way of spray coating, and after the surface is dried, an acetylsalicylic acid coating having a thickness of 5 μm is manufactured, which completely covers the surface of the stent. Then a poly-dl-lactic acid-ethyl acetate (-sirolimus) solution having a molecular weight of 200,000 completely covers the surface of the acetylsalicylic acid coating in the way of spray coating; after the surface is dried, an absorbable iron-based alloy stent with a poly-dl-lactic acid (-sirolimus) coating having a thickness of 6 μm is manufactured, wherein a mass ratio of poly-dl-lactic acid to sirolimus is 4 to 1. The stent is soaked in the PBS, which is 5 times the volume of the stent, at 37° C. After the stent is corroded in vitro for one week, a formed iron acetylsalicylate complex is fully dissolved in the solution, then the soaking solution is filtered with the water-based filtering film having the aperture of 0.22 μm, and the concentration of dissolved iron in filtrate is tested with the atomic absorption spectrometer, thereby the concentration of the iron acetylsalicylate complex in the physiological environment is 762 mg/L.

Embodiment 6

Micro pores in the surface of a hollow pure iron bone nail are filled with a sodium ethylenediamine tetramethylene phosphonate and polyvinylpyrrolidone mixture to manufacture an absorbable iron-based bone nail. A mass ratio of sodium ethylenediamine tetramethylene phosphonate to polyvinylpyrrolidone to iron is 0.4 to 0.1 to 1. The bone nail is soaked in the PBS, which is 5 times the volume of the bone nail, at 37° C. After the bone nail is corroded in vitro for one week, a formed iron ethylenediamine tetramethylene phosphonate complex is fully dissolved in the solution, then the soaking solution is filtered with the water-based filtering film having the aperture of 0.22 μm, and the concentration of dissolved iron in filtrate is tested with the atomic absorption spectrometer, thereby the concentration of the iron ethylenediamine tetramethylene phosphonate complex in the physiological environment is 206 mg/L.

Embodiment 7

A hollow pure iron duct is filled with a phenanthroline and sodium carboxymethylcellulose mixture, a mass ratio of phenanthroline to sodium carboxymethylcellulose to iron is 0.2 to 0.1 to 1, and the iron duct is woven into a stent. Micro pores are formed in the surface of the stent, and the surface is coated with a poly-dl-lactic acid-ethyl acetate solution, which completely covers the surface of an acetylsalicylic acid coating and has a molecular weight of 200,000, in a way of spray coating; after the surface is dried, an absorbable iron-based alloy stent with a poly-dl-lactic acid coating having a thickness of 4 μm is manufactured. The stent is soaked in the PBS, which is 5 times the volume of the stent, at 37° C. After the stent is corroded in vitro for one week, a formed phenanthroline iron complex is fully dissolved in the solution, then the soaking solution is filtered with the water-based filtering film having the aperture of 0.22 μm, and the concentration of dissolved iron in filtrate is tested with the atomic absorption spectrometer, thereby the concentration of the phenanthroline iron complex in the physiological environment is 119 mg/L.

Embodiment 8

Micro pores in the surface of a hollow pure iron bone nail are filled with a 4,5-dioxybenzene-1,3-sodium disulfonate and sodium carboxymethylcellulose mixture to manufacture an absorbable iron-based bone nail. A mass ratio of 4,5-dioxybenzene-1,3-sodium disulfonate to sodium carboxymethylcellulose to iron is 0.4 to 0.1 to 1. The bone nail is soaked in the PBS, which is 5 times the volume of the bone nail, at 37° C. After the bone nail is corroded in vitro for one week, a formed 4,5-dioxybenzene-1,3-iron disulfonate complex is fully dissolved in the solution, then the soaking solution is filtered with the water-based filtering film having the aperture of 0.22 μm, and the concentration of dissolved iron in filtrate is tested with the atomic absorption spectrometer, thereby the concentration of the 4,5-dioxybenzene-1,3-iron disulfonate complex in the physiological environment is 276 mg/L.

Embodiment 9

The surface of a pure iron stent is coated with a layer of 5-methyl-2-methyl mercaptobenzoate and sodium carboxymethylcellulose mixed coating in a way of spray coating, and a mass ratio of 5-methyl-2-methyl mercaptobenzoate to sodium carboxymethylcellulose to iron is 0.2 to 0.1 to 1; then the outermost layer of the stent is coated with a poly-dl-lactic acid-ethyl acetate solution which has a molecular weight of 200,000 in the way of spray coating; after the outermost layer is dried, an absorbable iron-based stent with a poly-dl-lactic acid coating having a thickness of 4 μm is manufactured. The stent is soaked in the PBS, which is 5 times the volume of the stent, at 37° C. After the stent is corroded in vitro for one week, a formed iron complex is fully dissolved in the solution, then the soaking solution is filtered with the water-based filtering film having the aperture of 0.22 μm, and the concentration of dissolved iron in filtrate is tested with the atomic absorption spectrometer, thereby the concentration of the iron complex in the physiological environment is 89 mg/L.

Embodiment 10

A groove is formed in the surface of a pure iron bone nail, and then is filled with a 1-nitroso-2-naphthol-6-sodium sulfonate and starch mixed coating, and the mass ratio of 1-nitroso-2-naphthol-6-sodium sulfonate to starch to iron is 0.1 to 00.1 to 1. The bone nail is soaked in the PBS, which is 5 times the volume of the bone nail, at 37° C. After the bone nail is corroded in vitro for one week, a formed iron complex is fully dissolved in the solution, then the soaking solution is filtered with the water-based filtering film having the aperture of 0.22 μm, and the concentration of dissolved iron in filtrate is tested with the atomic absorption spectrometer, thereby the concentration of the 1-nitroso-2-naphthol-6-iron sulfonate complex in the physiological environment is 120 mg/L.

Embodiment 11

Micro pores in the surface of a hollow-structured pure iron bone nail with the mass of 0.3 g are filled with a sulfosalicylic acid and polyvinylpyrrolidone mixture to manufacture an absorbable iron-based bone nail. A mass ratio of sulfosalicylic acid to polyvinylpyrrolidone to iron is 0.4 to 0.1 to 1. The bone nail is soaked in 100 mL of the PBS at 37° C. After the bone nail is corroded in vitro for one week, a formed sulfosalicylic iron complex is fully dissolved in the solution, then the soaking solution is filtered with the water-based filtering film having the aperture of 0.22 μm, and the concentration of dissolved iron in filtrate is tested with the atomic absorption spectrometer, thereby the concentration of the sulfosalicylic iron complex in the physiological environment is 174 mg/L.

Contrast 1

A pure iron bone nail with the mass of 1.2 g is soaked in 100 mL of the PBS at 37° C. After the bone nail is corroded in vitro for one week, the soaking solution is filtered with the water-based filtering film having the aperture of 0.22 μm, and the concentration of dissolved iron in filtrate is tested as 0 mg/L with the atomic absorption spectrometer.

By comparison between the embodiments from 1 to 11 and Contrast 1, the absorbable implanted medical devices having the complex bodies of all the embodiments all generate the water-soluble iron complexes which have solubility greater than 10 mg/L in the physiological environment, but the device of Contrast 1 generates an insoluble corrosion product which is hard to metabolize in the physiological environment,\. In contrast, the solubility of the iron complex generated in Embodiment 2 is relatively low, thus leading to sedimentation of part of the iron complex. However, under the physiological environment, with gradual diffusion of the dissolved iron complex, the iron complex sedimentation portion may be gradually dissolved, and can be finally completely dissolved and diffused and then absorbed/metabolized. Therefore, the embodiments from 1 to 11 reduce generation of the insoluble solid corrosion products, and corrosion products of the iron-based alloy substrate are easy to metabolize/absorb.

The above embodiments only express several implementation modes of the present application, and their descriptions are relatively specific and detailed, but they are not intended to limit the scope of patent of the present application thereby. It should be noted that a person skilled in the art can make various deformations and improvements without departing from the concept of the present application, and these deformations and improvements shall all fall within the scope of protection of the present application. Thus, attached claims for the scope of protection of the present application shall prevail.

The invention claimed is:

1. An absorbable pure iron or iron alloy implanted medical device, comprising:
   a pure iron or an iron alloy substrate, and a complex body, wherein the complex body comprises as a complexing agent a polydentate ligand,
   wherein the polydentate ligand is selected from the group consisting of:
   a hydroxyl-on-polycyclic aromatic hydrocarbon-containing polydentate ligand selected from the group consisting of 8-hydroxyquinoline, 8-hydroxyquinaldine, 4,5-dioxybenzene-1,3- sodium disulfonate, and 4-[3,5-bis-hydroxyphenyl-1H-1,2,4-triazole]-benzoic acid;
   a sulfydryl group-containing polydentate ligand selected from the group consisting of 8-mercaptoquinoline, mercaptoacetic acid, and 5-methyl-2-mercapto mercaptobenzoate;
   an amido-containing polydentate ligand selected from the group consisting of ethidene diamine, and triethylene tetramine;
   a hetero aromatic group-containing polydentate ligand selected from the group consisting of phenanthroline, dipyridyl, porphyrin, porphin, chlorophyll, hemoglobin, and 1,2-dimethyl-3-hydroxyl-4-pyridone;
   a nitroso-containing polydentate ligand selected from the group consisting of 1-nitroso-2-naphthol and 1-nitroso-2-naphthol-6-sodium sulfonate;
   a carbonyl-containing polydentate ligand selected from the group consisting of oxalic acid, oxaloacetic acid, nitrilotriacetic acid, diethylene triamine penta(carboxylic acid), alginic acid, potassium citrate, calcium citrate, monoglyceride citrate, acetylsalicylic acid, sulpho salicylamide, polyaspartic acid, polyglutamic acid, poly-ornithine, polylysine, and polymaleic anhydride; a sulpho-containing polydentate ligand selected from the group consisting of sulfosalicylic acid and 8-hydroxy-quinoline-5-sulphonic acid;
   a phosphate group-containing polydentate ligand selected from the group consisting of pyrophosphoric acid, tripolyphosphoric acid, hexadecophosphoric acid, polyphosphoric acid, sodium pyrophosphate, sodium hexametaphosphate, and ammonium polyphosphate;
   wherein, in a physiological solution, the pure iron or iron alloy substrate reacts with the complexing agent to generate a water-soluble iron complex which has a solubility greater than or equal to 10 mg/L in the physiological solution after being corroded in vitro for one week.

2. The absorbable pure iron or iron alloy implanted medical device according to claim 1, further comprising a degradable polymer layer, wherein the degradable polymer layer comprises an active drug which is selected from the group consisting of a drug for inhibiting vascular proliferation, an antiplatelet drug, an antithrombotic drug, an anti-inflammatory reaction drug, and an antisensitization drug;
   the drug for inhibiting vascular proliferation is selected from at least one of taxol, sirolimus, and a derivative thereof;
   the antiplatelet drug is cilostazol;
   the antithrombotic drug is heparin;
   the anti-inflammation reaction drug is dexamethasone; and
   the antisensitization drug is selected from at least one of calcium gluconate, chlortrimeton, and cortisone.

3. The absorbable pure iron or iron alloy implanted medical device according to claim 1, further comprising an adhesive and a thickener, wherein the adhesive is selected from at least one of polyethylene glycol, polyvinyl alcohol, starch, cyclodextrin, and water-soluble inorganic salt; and
   the thickener is selected from at least one of gelatin, polyvinylpyrrolidone (PVP), and sodium carboxymethylcellulose (CMC).

4. The absorbable pure iron or iron alloy implanted medical device according to claim 1, wherein the pure iron or iron alloy substrate is pure iron.

5. The absorbable pure iron or iron alloy implanted medical device according to claim 1, wherein the pure iron or iron alloy substrate is an iron alloy with a carbon content less than or equal to 2.11 wt. %.

6. The absorbable pure iron or iron alloy implanted medical device according to claim 1, the complex body further comprising an adhesive and/or thickener, and the volume percentage of the complexing agent is greater than or equal to 10 percent but less than 100 percent.

7. The absorbable pure iron or iron alloy implanted medical device according to claim 1, wherein the complex body is disposed on the surface of or inside the iron alloy substrate.

8. The absorbable pure iron or iron alloy implanted medical device according to claim 1, further comprising a degradable polymer layer which is selected from degradable polyester and/or degradable polyanhydride;
   the degradable polyester is one of polylactic acid, polyglycolic acid, poly(lactic acid-glycolic acid), polycaprolactone, polyhydroxyalkanoate, polyacrylate, poly(ethylene succinate), poly(β-hydroxybutyrate), and polyethylene glycol adipate, or is a physical blend of at least two of the polylactic acid, the polyglycolic acid, the poly(ethylene succinate), the poly(β-hydroxybutyrate), the polycaprolactone, the polyethylene glycol adipate, a polylactic acid- glycollic acid copolymer, and a polyhydroxybutyrate-pentanoate copolymer, or is any one of copolymers formed by copolymerizing at least two of monomers forming the polylactic acid, the polyglycolic acid, the poly(ethylene succinate), the poly(β-hydroxybutyrate), the polycaprolactone, the polyethylene glycol adipate, the polylactic acid-glycollic acid copolymer, and the polyhydroxybutyrate-pentanoate copolymer;

the degradable polyanhydride is selected from at least one of poly1,3-bis(p-carboxyphenoxy)propane-sebacic acid, poly(erucic acid dimer-sebacic acid), and poly(fumaric acid-sebacic acid), or is a physical blend of at least two of the poly1,3-bis(p-carboxyphenoxy)propane-sebacic acid, the poly(erucic acid dimer-sebacic acid), or the poly(fumaric acid-sebacic acid), or any one of copolymers formed by copolymerizing at least two of monomers forming the poly1,3-bis(p-carboxyphenoxy)propane-sebacic acid, the poly(erucic acid dimer-sebacic acid), and the poly(fumaric acid-sebacic acid); or the degradable polymer is a copolymer formed by copolymerizing at least two of monomers forming the degradable polyester and the degradable polyanhydride.

* * * * *